United States Patent [19]
Iizuka et al.

[11] Patent Number: 4,711,958
[45] Date of Patent: Dec. 8, 1987

[54] MORPHOLINE CONTAINING AMINO ACID DERIVATIVES

[75] Inventors: Kinji Iizuka; Tetsuhide Kamijo; Tetsuhiro Kubota; Kenji Akahane, all of Nagano; Hideaki Umeyama, Chiba; Yoshiaki Kiso, Osaka, all of Japan

[73] Assignee: Kissei Pharmaceutical Co., Ltd., Nagano, Japan

[21] Appl. No.: 32,693

[22] Filed: Apr. 1, 1987

[30] Foreign Application Priority Data

Apr. 1, 1986 [JP] Japan .................................. 61-74511
Jul. 10, 1986 [JP] Japan ................................ 61-162563

[51] Int. Cl.$^4$ .......................................... C07D 295/18
[52] U.S. Cl. ..................................... 544/139; 544/82; 560/125; 564/191
[58] Field of Search ..................... 544/82, 139

[56] References Cited

U.S. PATENT DOCUMENTS 4,656,269  4/1987  Iizuka et al. ..................... 544/139

Primary Examiner—Robert W. Ramsuer
Attorney, Agent, or Firm—Sughrue, Mion, Zinn, Macpeak & Seas

[57] ABSTRACT

Amino acid derivatives represented by formula

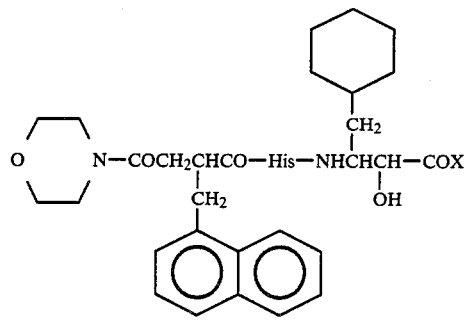

wherein His represents an L-histidyl group, X represents a straight or branched alkoxy group having 1 to 7 carbon atoms, a straight or branched alkylamino group having 1 to 7 carbon atoms, a cycloalkyloxy group having 3 to 7 carbon atoms, a morpholino group, said alkoxy group having one or more halogen atoms as substituents; or a pharmaceutically acceptable salt, are useful in the treatment of hypertension.

3 Claims, No Drawings

MORPHOLINE CONTAINING AMINO ACID DERIVATIVES

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially reninassociated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contracts the vascular smooth muscle and acts on the adrenal cortex to secrete the aldosterone which regulates salts and water balance. Accordingly, the reninangiotensin system plays an important role in hypertension. An effective inhibitor of renin has long been sought as an agent for treatment of hypertension, especially renin-associated hypertension. As a result, it has been found that certain peptides show a renin inhibitory effect, as described in U.S. Pat. No. 4,548,926, Japanese patent application (OPI) Nos. 163899/85, 275257/86, 78795/86, 227851/84, 155345/84, 110661/84, (The term "OPI" as used herein refers to an unexamined Japanese patent application).; Japanese patent publication No. 39149/83, Biochemical and Biophysical Research Communications, Vol. 118, pages 929-933, 1984; and European patent application Nos. 77029(A2), 77028(A2) and 81783(A2).

Of these prior art references, Japanese patent application (OPI) No. 163899/85 discloses peptides represented by the following formula:

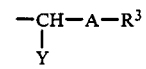

wherein
$R^1CO$ represents an aliphatic acyl group, an aromatic acyl group, an aromatic aliphatic acyl group, a heterocyclic acyl group or a heterocyclic aliphatic acyl group, said acyl groups being able to have an amino group, a protected amino group, a hydroxy group, a substituted a dithio group, an alkyl group, an alkoxy group, an alkoxycarbonyl group, a halogen atom or a nitro group as a substituent;

$R^2$ represents an isobutyl group or a sec-butyl group;
X represents a group of formula

in which $R^3$ represents a carboxyl group, and substituted carbamoyl group, a carbazoyl group, an N-substituted carbazoyl group or an acyl group, A represents a single bond or an alkylene group, Y represents a hydroxy group, a mercapto group or a formyl group, or a group of formula $$-\overset{O}{\underset{OH}{\overset{\|}{P}}}-R^4$$

in which $R^4$ represents a substituted alkyl group having a carboxyl group, a protected carboxy group, an N-substituted carbamoyl group, a carbazoyl group, an N-substituted carbazoyl group or an acyl group as a substituent;

His represents an L-histidyl group;
and pharmaceutically acceptable salts and esters thereof.

Japanese patent application (OPI) No. 78795/86 also discloses optical isomers of peptides disclosed in Japanese patent application (OPI) No. 163899/85.

Japanese patent application (OPI) No. 275257/86 discloses peptides closely related to compounds of this invention. Although this reference does not specifically disclose, the compounds having following formula is included within the broad scope thereof:

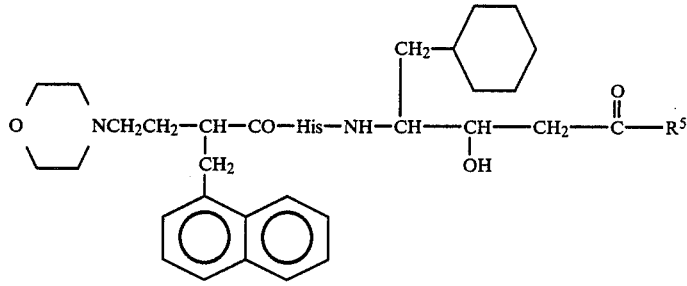

wherein $R^5$ represents an alkoxy group having 1 to 10 carbon atoms, a mono or di-alkylamino group having 1 to 10 carbon atoms or a heterocyclic group, said heterocyclic group being connected the carbonyl group in the formula with the nitrogen atom in said heterocyclic group, and pharmaceutically acceptable salts thereof.

However, this reference does not teach that compounds having a morpholinocarbonylmethyl group instead of the morpholinoethyl group exhibit an excellent renin inhibitory activity.

Furthermore, with regard to peptides related to those of this invention, the inventors of this invention also have filled some U.S. patent applications Ser. Nos. 789,597 (filed Oct. 21, 1985), 824,341 (filed Jan. 31, 1986), 852,260 (filed Apr. 15, 1986), now U.S. Pat. No. 4,656,269, 879,741 (filed June 27, 1986) and 903,803 (filed Sept. 14, 1986).

On the other hand, by someone of the present inventors and others, analogous peptides to those of this invention have been published in European Journal of Pharmacology Vol. 129, No. 3, 393-396, 1986, and have been reported in the 50th Annual Scientific Meeting of the Japanese Circulation Society, March, 1986, the 59th General Meeting of the Japanese Pharmacological Society, April, 1986, the 106th Annual Meeting of Pharmaceutical Society of Japan, April, 1986, the 37th Regional Meeting (Kita area) of the Japanese Pharmacological Society, August, 1986.

SUMMARY OF THE INVENTION

An object of this invention is to provide new amino acid derivatives which exhibit a specific inhibitory effect on renin when administered orally to mammalia including humans.

Another object of this invention is to provide new amino acid derivatives and pharmaceutically acceptable salts thereof.

A further object of this invention is to provide pharmaceutical compositions comprising new amino acid derivatives or pharmaceutically acceptable salts thereof.

A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

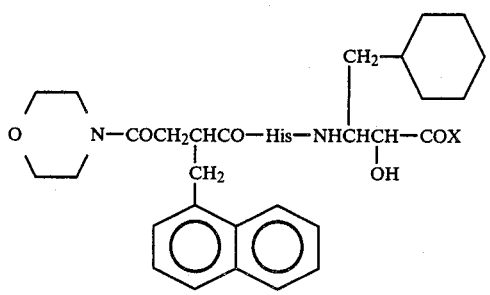

wherein His represents an L-histidyl group, X represents a straight or branched alkoxy group having 1 to 7 carbon atoms, a straight or branched alkylamino group having 1 to 7 carbon atoms, a cycloalkyloxy group having 3 to 7 carbon atoms, a morpholino group or said alkoxy group having one or more halogen atoms as substituents; or pharmaceutically acceptable salts thereof.

DETAILED DESCRIPTION OF THE INVENTION

The amino acid derivatives of formula (I) of this invention and pharmaceutically acceptable salts thereof exhibit an renin inhibitory activity in a human renin-sheep renin substrate system and human plasma renin activity. Furthermore, the amino acid derivatives of this invention are stable against proteolytic enzymes such as pepsin and chymotrypsins.

These findings demonstrate that the amino acid derivatives of formula (I) of this invention exhibit a human renin inhibitory effect when administered orally to mammalia, including humans, and thus are useful for treatment of hypertension, especially renin-associated hypertension.

The amino acid derivatives of formula (I) of this invention can be prepared according to well-known methods. That is, the amino acid derivatives of this invention represented by formula (I):

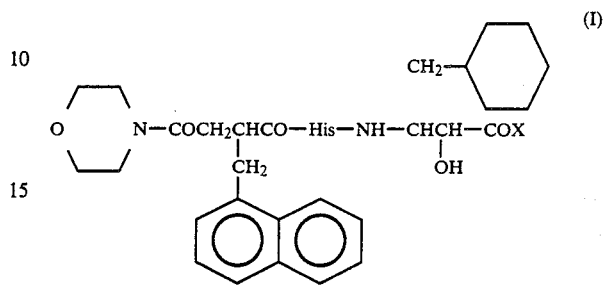

wherein His and X have the same meanings as defined above, can be prepared by reacting a compound represented by formula (II):

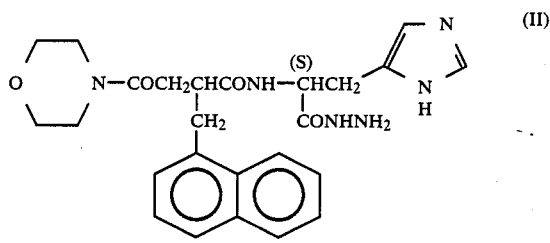

wherein (S) represents S-configuration, with a compound represented by formula (III):

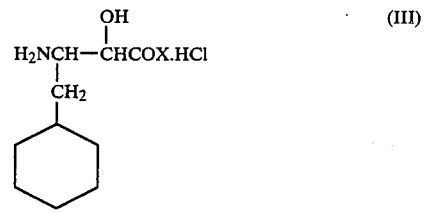

wherein X has the same meaning as defined above, or by reacting a compound representd by formula (IV):

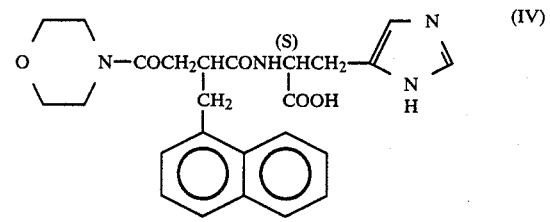

wherein (S) has the same meaning as defined above, with the compound of formula (III) above in the presence of a condensing agent.

The compounds of formulae (II) and (IV) as starting materials can be prepared by an analogous method to that described in Japanese patent application (OPI) 236770/86.

The compounds represented by formula (III) used as another starting material can be prepared in an analogous method to that described in the literature.

The compound represented by formula (III) can be prepared by hydrogenating N-(tert-butoxycarbonyl)-L-phenylalanine over rhodium on alumina powder, reducing the obtained N-(tert-butoxycarbonyl)-L-cyclohexylalanine in the presence of a reducing agent such as a borane compound, treating the obtained N-(tert-butoxycarbonyl)-L-cyclohexylalaninol with pyridine sulfur trioxide complex in dimethyl sulfoxide in the presence of triethylamine, reacting the obtained N-(tert-butoxycarbonyl)-L-cyclohexylalaninal with potassium cyanide, and hydrolyzing the resultant compound, and then esterifying or amidating the amino acid derivative obtained by conventional method.

The reaction of the compound represented by formula (II) and the compound of formula (III) can be carried out according to a usual manner.

That is, the amino acid derivative of formula (I) of this invention can be prepared by suspending the compound of formula (II) in N,N-dimethylformamide, passing hydrogen chloride in a proportion of from about 3 to about 5 molar amounts per mole of the compound of formula (II) into the suspension, adding isoamyl nitrite in a proportion of from about 1 to about 3 molar amounts per mole of the compound of formula (II) to the mixture, reacting the mixture for about 5 to about 30 minutes at about −20° C. to about −5° C., and adjusting a pH of the reaction mixture to about 8 to about 9 by addition of triethylamine. The mixture is added dropwise to a solution of the compound of formula (III) and triethylamine in an equimolar amount to the compound of formula (II) in N,N-dimethylformamide under ice-cooling, preferably −20° C. to 0° C., and the mixture is treated for about 5 to about 20 hours at 0° C. to room temperature. To the reaction mixture was added a 5% aqueous sodium bicarbonate solution, followed by extracting with ethyl acetate, evaporating the ethyl acetate layer, and then purifying the residue by preparative silica gel thin layer chromatography, silica gel flash column chromatography or high performance liquid chromatography.

The reaction of the compound represented by formula (III) and the compound represented by formula (IV) can also be preferably carried out by dissolving the compound represented by formula (IV) in N,N-dimethylformamide, adding 1-hydroxybenzotriazole and dicyclohexylcarbodiimide, and reacting the mixture for 10 to 20 hours at room temperature, and then treating the reaction mixture according to a usual manner to obtain the desired compound.

The amino acid derivatives represented by formula (I) of this invention contain four asymmetric carbon atoms including one in the L-histidine moiety, and therefore, various stereoisomers of the amino acid derivatives exist depending upon the configuration of each asymmetric carbon atoms. Although configurations of the asymmetric carbon atoms affect the renin inhibitory activity of the compound represented by formula (I), the configurations of the asymmetric carbon atoms other than that of the L-histidine moiety are not limited in this invention with respect to these isomers.

In the amino acid derivatives represented by formula (I), the configuration of the carbon atom on which the amino group is substituted in the moiety of the compound represented by formula (III) is preferably S-configuration, whereas the configuration of the carbon atom on which the hydroxy group is substituted in the above moiety affects the activity. R-configuration is preferable, but a mixture of S- and R-configuration can be employed.

The optically active starting materials used for preparation of those optically active compounds can be prepared by performing an optical resolution according to a usual manner or using an optically active compound.

The amino acid derivatives represented by formula (I) of this invention can be converted according to conventional methods into pharmaceutically acceptable salts thereof. Examples of such pharmaceutically acceptable salts include pharmaceutically acceptable inorganic or organic acid salts such as a hydrochloric acid salt, a sulfuric acid salt, a p-toluenesulfonic acid salt, an acetic acid salt, a citric acid salt, tartaric acid salt, a succinic acid salt, a fumaric acid salt and the like. These salts have a renin inhibitory effect as high as the corresponding compound having a free amino group and are stable against proteolytic enzymes, and thus they show the desired renin inhibitory effect even by oral administration.

The amino acid derivatives represented by formula (I) of the present invention possess a strong inhibitory effect on human renin, for example, the amino acid derivatives of formula (I) produce a 50% inhibition in human renin-sheep substrate system and in human high renin plasma at $3.7 \times 10^{-7}$ to $2.4 \times 10^{-9}$ and $2.6 \times 10^{-7}$ to $4.1 \times 10^{-9}$ molar concentrations, respectively, and reduce blood pressure of marmosets in a high renin state with a low toxicity, and thus are useful as a therapeutically active agent for treatment of hypertension, especially renin-associated hypertension.

The amino acid derivatives represented by formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salts of the formula (I) of this invention can be administered in various dosage forms depending upon the intended therapy. Typical dosage forms which can be used are tablets, pills, powders, liquid preparations, suspensions, emulsions, granules, capslues, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of this invention may be in the range from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following Examples, Reference Examples, Text Example. The melting points of the product obtained were uncorrected. The NMR spectra of the products were measured by JEOL's High Resolution NMR Spectrometer Type JNM-GX 270. The Mass spectra of the products were measured by JEOL's Mass Spectrometer Type JMS-DX 300 according to the FAB method. Thin layer chromatography was carried out using Merck's precoated plates silica gel 60 $F_{254}$ and column chromatography was carried out by employing Merck's Kiesel gel 60 (230–400 mesh). Thin layer chromatography was carried out by using a lower layer of a mixture of chloroform, methanol and water in a proportion of 8/3/1 (by volume) (mixture A) and mixture of chloroform and methanol in a proportion of 5/1 (by volume) (mixture B) as eluent, and an $Rf_1$ (mixture A) value and $Rf_2$ (mixture B) value were calculated.

REFERENCE EXAMPLE 1

2-(1-Naphthylmethyl)-3-(morpholinocarboyl)propionic acid

To a solution of 32.3 g of ethyl succinate and 29.0 g of 1-naphthaldehyde in 320 ml of absolute ethyl alcohol was added 10.7 g of a 50% sodium hydride (dispersion in mineral oil) with stirring under ice-cooling, and then the mixture was heated under reflux for 30 minutes. To the reaction mixture was added 230 ml of a 2N-aqueous sodium hydroxide soluiton, and then the mixture was heated under reflux for an hour. The reaction mixture was evaporated under reduced pressure, and to the residue was added water. The mixture was extracted with ethyl ether to remove neutral materials. The aqueous layer was acidified by adding concentrated hydrochloric acid, and then extracted with ethyl ether. The ethereal layer was washed with a saturated sodium chloride aqueous solution, dried over anhydrous magnesium sulfate, and evaporated under reduced pressure. Benzene was added to the residue, and the precipitated crystals were collected by filtration to obtain 26.5 g of 2-(1-naphthylmethylene)succinic acid as yellow crystals.

A mixture of 24.5 g of 2-(1-naphthylmethylene)succinic acid and 260 ml of acetic anhydride was heated at 60° C. for an hour, and then the reaction mixture was evaporated under reduced pressure. To the residue was added a mixture of benzene and hexane (1/1, by volume). The precipitated crystals were collected by filtration to obtain 16.0 g of 2-(1-naphthylmethylene)succinic anhydride as orange-yellow crystals.

The solution of 1.00 g of the 2-(1-naphthylmethylene)succinic anhydride and 0.37 g of morpholine in 31 ml of dry dichloromethane was stirred for 2 hours at room temperature. The reaction mixture was evaporated under reduced pressure, and the residue was triturated with a mixture of ethyl acetate, benzene and hexane (1/1/1 by volume) to obtain 1.10 g of 2-(1-naphthyl-methylene)-3-(morpholinocarbonyl)propionic acid as colorless crystals.

A mixture of 1.00 g of the acid and 0.1 g of a 10% palladium charcoal in 40 ml of methyl alcohol was hydrogenated under atmospheric pressure. After filtration of the catalyst, the filtrate was evaporated under reduced pressure, and the residue was triturated with hexane to obtain 0.90 g of 2-(1-naphthylmethyl)-3-(morpholinocarbonyl)propionic acid as a white powder.

$Rf_1$: 0.67
MS: MH+, 328
melting point: 64°–68° C.
IR (KBr): $\nu$co 1720, 1640 cm$^{-1}$
NMR (CDCl$_3$) $\delta$: 2.35–2.7(m, 2H), 3.05–3.85(m, 11H), 7.25–8.2(m, 7H)

REFERENCE EXAMPLE 2

N-[2-(1-Naphthylmethyl)-3-(morpholinocarbonyl)propionyl]-L-histidine hydrazide

To a suspension of 0.89 g of 2-(1-naphthylmethyl)-3-(morpholinocarbonyl)propionic acid and 0.79 g of L-histidine methyl ester dihydrochloride in 23 ml of N,N-dimethylformamide were added 0.70 ml of diphenylphosphoryl azide and 1.50 ml of triethylamine with stirring under ice-cooling, and then the mixture was additionaly stirred for 16 hours. The reaction mixture was evaporated under reduced pressure, and to the residue was added a 5% aqueous sodium bicarbonate solution. The mixture was extracted with ethyl acetate, and the ethyl acetate layer was washed with water, dried over anhydrous magnesium sulfate, and evaporated under reduced pressure. To the residue was added diethyl ether, and the precipitate was collected by filtration to obtain 1.25 g of N-[2-(1-naphthylmethyl)-3-(morpholinocarbonyl)propionyl]-L-histidine methyl ester as a white powder. To a soluiton of 0.98 g of the ester compound in 10 ml of methanol was added 0.52 g of hydrazide monohydrate, and then the mixture was stirred for 4 hours. The reaction mixture was evaporated under reduced pressure, and the residue was purified by silica gel column chromatography (eluent: chloroform/methanol=10/1 by volume) to obtain 0.23 g of N-[2-(1-naphthylmethyl)-3-(morpholinocarbonyl)propionyl]-L-histidine hydrazide having an $Rf_1$ value of 0.49 as a white powder.

melting point: 115°–119° C.
$Rf_1$: 0.49
MS: MH+, 479
IR (KBr): $\nu$co 1620 cm$^{-1}$

REFERENCE EXAMPLE 3

(3S)-3-Amino-4-cyclohexyl-2-hydroxybutyric acid isopropyl ester hydrochloride (2RS and 2R forms)

To a solution of 13.25 g of N-(tert-butoxycarbonyl)-L-phenylalanine in 25 ml of methanol was added 1.2 g of a 5% rhodium on alumina powder, and then mixture was hydrogenated under a pressure of 3.5 kg/cm². After filtration of the catalyst, the filtrate was evaporated under reduced pressure to obtain 13.4 g of N-(tert-butoxycarbonyl)-L-cyclohexylalamine as a white powder.

A mixture of 2.71 g of N-(tert-butoxycarbonyl)-L-cyclohexylalanine in 5 ml of dry tetrahydrofuran was added dropwise to 20 ml of a 1M boron tetrahydrofuran solution keeping a temperature at 5° C. to 8° C. under an atmosphere of argon, and then the mixture was still stirred for 3 hours. The reaction mixture was adjusted to a pH of 4 by adding a 10% acetic acid methanol solution, and the mixture was evaporated under reduced pressure. To the residue was added diethyl ether, and the mixture was washed successively with an aqueous citric acid solution, an aqueous sodium bicarbonate solution and a saturated sodium chloride aqueous solution, dried over anhydrous magnesium sulfate, and evaporated under reduced pressure to obtain 2.42 g of N-(tert-butoxycarbonyl)-L-cyclohexylalaninol.

A mixture of 2.4 g of N-(tert-butoxycarbonyl)-L-cyclohexylalaninol, 6.5 ml of dry triethyl amine, 3 ml of dry benzene and 6.6 ml of dry dimethyl sulfoxide was cooled to 15° C., and then 7.4 g of sulfur trioxide pyridine complex was added portionwise to the mixture keeping a temperature at 15° C. to 20° C. The mixture was still stirred for 10 minutes. The reaction mixture was poured into water, and the mixture was extracted with ethyl acetate. The ethyl acetate layer was washed successively with a saturated sodium bicarbonate aqueous solution and water, dried over anhydrous magnesium sulfate, and evaporated under reduced pressure to obtain 2.9 g of N-(tert-butoxycarbonyl)-L-cyclohexylalaninal.

A solution of 2.9 of sodium sulfite in 20 ml of water was added to 2.9 g of N-(tert-butoxycarbonyl)-L-cyclohexylalaninal, and the mixture was stirred for 14 hours under ice-cooling. To the reaction mixture was added a solution of 1.82 g of potassium cyanide in 5 ml of water and 40 ml of ethyl acetate, and then the mixture was stirred for 4 hours at room temperature. The ethyl acetate layer was washed with a saturated sodium chloride aqueous solution, dried over anhydrous magnesium sulfate, and evaporated under reduced pressure. To the residue was added 21 ml of a 23% hydrochloric acid, and the mixture was heated under reflux for 12 hours to obtain the reaction mixture [A].

Method 1 (2RS form)

The reaction mixture [A] was washed with diethyl ether, and the aqueous layer was evaporated under reduced pressure to obtain 2.5 g of (2RS, 3S)-3-amino-4-cyclohexyl-2-hydroxybutyric acid hydrochloride as a white powder.

Hydrogen chloride was passed into a solution of 100 mg of (2RS, 3S)-3-amino-4-cyclohexyl-2-hydroxybutyric acid hydrochloride in 12 ml of isopropyl alcohol with stirring under ice-cooling, and the mixture was heated under reflux for 2 hours. The reaction mixture was evaporated to dryness under reduced pressure, and the residue was purified by silica gel column chromatography (eluent: chloroform/methanol =15/1 by volume), and the eluate was acidified by adding hydrochloric acid. The mixture was evaporated to dryness under reduced pressure to obtain 108 mg of (2RS, 3S)-3-amino-4-cyclohexyl-2hydroxybutyric acid isopropyl ester hydrochloride as a white powder.

IR (KBr): νco 1735 cm$^{-1}$
NMR (D$_2$O) δ:0.8–1.8(m, 19H), 3.6–3.8(m, 1H), 4.3–4.6(m, 1H), 5.0–5.2(m, 1H)

Method 2 (2R form)

The reaction mixture [A] was washed with toluene, and the aqueous layer was evaporated to about 30 ml under reduced pressure. The solution was allowed to stand overnight, and the precipitated crystals were collected by filtration and washed with toluene to obtain 1.0 g of (2R, 3S)-3-amino-4-cyclohexyl-2-hydroxybutyric acid hydrochloride as a white powder.

Hydrogen chloride was passed into a suspension of 1.0 g of (2R, 3S)-3-amino-4-cyclohexyl-2-hydroxy butyric acid hydrochloride in 10 ml of isopropyl alcohol with stirring under ice-cooling, and the mixture was heated under reflux for 2 hours. After evaporation of the reaction mixture, benzene was added to the residue and the mixture was evaporated under reduced pressure. The residue was dissolved in 10 ml of ethyl acetate and the precipitated crystals were collected by filtration to obtain 1.0 g of (2R, 3S)3-amino-4-cyclohexyl-2-hydroxybutyric acid isopropyl ester hydrochloride as a white powder.

melting point: 113°–115° C.
IR (KBr): νco 1720 cm$^{-1}$
MNR (D$_2$O) δ:0.8–1.8(m, 19H), 3.6–3.8(m, 1H), 4.37(d, 1H, J=4.9Hz), 5.0–5.2(m, 1H)

REFERENCE EXAMPLE 4

(2RS, 3S)-3-Amino-4-cyclohexyl-2-hydroxy-N-isobutylbutyramide hydrochloride

In a mixture of 10 ml of water and 10 ml of dioxane were dissolved 1.4 g of (2RS, 3S)-3-amino-4-cyclohexyl-2-hydroxybutyric acid hydrochloride and 1.64 ml of triethylamine, and to the solution was added 3.2 g of di-tert-butyldicarbonate. The mixture was stirred for 16 hours at room temperature, and to the reaction mixture was added 20 ml of water. The mixture was extracted with diethyl ether to remove neutral materials. The aqueous layer was acidified by adding an aqueous citric acid solution, and then extracted with diethyl ether. The ethereal layer was washed with a saturated sodium chloride aqueous solution, dried over anhydrous magnesium sulfate, and evaporated under reduced pressure to obtain 0.9 g of (2RS, 3S)-3-tert-butoxycarbonylamino-4-cyclohexyl-2-hydroxybutyric acid as a colorless oil.

To a solution of 400 mg of the butyric acid compound, 175 mg of isobutylamine hydrochloride, 270 mg of 1-hydroxybenzotiazole and 0.22 ml of triethylamine in 20 ml of ethyl acetate was added 300 mg of dicyclohexylcarbodiimide with stirring under ice-cooling, and then the mixture was still stirred for 16 hours. The reaction mixture was cooled, and filtered to remove insoluble materials. The filtrate was washed successively with an aqueous citric acid solution, a 5% aqueous sodium bicarbonate solution and a saturated sodium chloride aqueous solution, dried over anhydrous magnesium sulfate, and evaporated under reduced pressure to obtain 595 mg of (2RS, 3S)-3-(tert-butoxycarbonyl)amino-4-cyclohexyl-2-hydroxy-N-isobutylbutyramide.

To a solution of 590 mg of the amide compound in 10 ml of methyl alcohol was added 3.3 ml of a 2N-hydrochloric acid, and the mixture was heated under reflux for 2 hours. The reaction mixture was evaporated under reduced pressure to obtain 254 mg of (2RS, 3S)-3-amino-4-cyclohexyl-2-hydroxy-N-isobutylbutyramide hydrochloride as a white powder.

IR (KBr): νco 1640 cm$^{-1}$
NMR (D$_2$O) δ: 0.8–2.0(m, 2H), 2.9–3.2(m, 2H), 3.5–3.7(m, 1H), 4.2–4.5(m, 1H)

REFERENCE EXAMPLE 5

N-[2-(1-Naphthylmethyl)-3-(morpholinocarbonyl)propionyl]-L-histidine methyl ester To a suspension of 0.89 g of 2-(1-naphthylmethyl)3-(morpholinocarbonyl)propionic acid and 0.79 g of L- histidine methyl ester dihydrochloride in 23 ml of N,N-dimethylformamide were added 0.70 ml of diphenylphosphoryl azide and 1.50 ml of triethylamine with stirring under ice-cooling, and then the mixture was additionaly stirred for 16 hours. The reaction mixture was evaporated under reduced pressure, and to the residue was added a 5% aqueous sodium bicarbonate solution. The mixture was extracted with ethyl acetate, and the ethyl acetate layer was washed with water, dried over anhydrous magnesium sulfate, and evaporated under reduced pressure. The residue was purified by silica gel column chromatography (eluent: chloroform/methanol=20/1, by volume) to obtain 0.25 g of N-[2-(1-Naphthylmethyl)-3-(morpholinocarbonyl)propionyl]-L-histidine methyl ester having an $Rf_2$ value of 0.56 as a white powder.

Recrystallization of 0.25 g of the methyl ester from benzene was made to obtain 0.20 g of N-[2-(1-naphthylmethyl)-3-(morpholinocarbonyl)propionyl]-L-histidine methyl ester containing one mole of benzene as colorless needles.

$Rf_1$: 0.61
$Rf_2$: 0.56
IR (KBr): $\nu$co 1755, 1630, 1610 cm$^{-1}$

REFERENCE EXAMPLE 6

(2RS, 3S)-3-Amino-4-cyclohexyl-2-hydroxybutyric acid cyclopentyl ester hydrochloride Hydrogen chloride was passed into a solution of 300 mg of (2RS, 3S)-3-amino-4-cyclohexyl-2-hydroxybutyric acid hydrochloride, which was prepared in Reference Example 2, in 5 ml of cyclopentyl alcohol with stirring under ice-cooling, and then the mixture was heated at 90° C. for 5 hours. The reaction mixture was evaporated under reduced pressure, and the residue was purified by silica gel column chromatography (eluent: chloroform/methanol=15/1 by volume). The eluate was acidified by adding hydrochloric acid, and then evaporated to dryness under reduced pressure to obtain 380 mg of (2RS, 3S)-3-amino-4-cyclohexyl-2hydroxybutyric acid cyclopentyl ester hydrochloride as a white powder.

IR (KBr): $\nu$co 1730 cm$^{-1}$
NMR (D$_2$O) δ: 0.8–2.0(m, 21H), 3.6–4.0(m, 1H), 4.3–4.7(m, 1H), 5.2–5.4(m, 1H)

REFERENCE EXAMPLE 7

The following ester compounds were prepared in an analogous manner to that described in Reference Examples 2 and 6.

(2RS, 3S)-3-Amino-4-cyclohexyl-2-hydroybutyric acid cyclohexyl ester hydrochloride Viscous colorless oil
IR (neat): $\nu$co 1730 cm$^{-1}$
NMR (D$_2$O) δ: 0.8–2.0(m, 23H), 3.5–4.0(m, 1H), 4.3–4.7(m, 1H), 4.8–5.0(m, 1H)

(2RS, 3S)-3-Amino-4-cyclohexyl-2-hydroxybutyric acid 1,3-difluoro-2-propyl ester White powder
IR (KBr): $\nu$co 1735 cm$^{-1}$
NMR (CDCl$_3$) δ: 0.8–2.0 (m, 13H), 3.3–3.9 (m, 1H), 4.1–5.0(m, 5H), 5.2–5.6(m, 1H)

REFERENCE EXAMPLE 8

4-[(2RS, 3S)-3-Amino-4-cyclohexyl-2-hydroxybutyryl]morpholine hydrochloride

To a solution of 200 mg of (2RS, 3S)-3-tertbutoxycarbonylamino-4-cyclohexyl-2-hydroxybutyric acid which was prepared in Reference Example 4, 0.06 ml of morpholine and 13 mg of 1-hydroxybenzotriazole in 6 ml of ethyl acetate was added 150 mg of dicyclohexylcarbodiimide with stirring under ice-cooling, and the mixture was stirred for 16 hours at room temperature. The reaction mixture was cooled, and filtered to remove insoluble materials. The filtrate was washed successively with an aqueous citric acid solution, a 5% aqueous sodium bicarbonate solution and a saturated sodium chloride aqueous solution, dried over anhydrous magnesium sulfate, and evaporated under reduced pressure to obtain 296 mg of 4-[(2RS, 3S)-3-(tertbutoxycarbonyl)amino-4-cyclohexyl-2-hydroxybutyryl]morpholine.

To a solution of 290 mg of the amide compound in 5 ml of methyl alcohol was added 1.0 ml of a 2N-hydrochloric acid, and the mixture was heated under reflux for 3 hours. The reaction mixture was evaporated under reduced pressure to obtain 206 mg of 4-[(2RS, 3S)-3-amino-4-cyclohexyl-2-hydroxybutyryl]morpholine hydrochloride as a white powder.

IR (KBr): $\nu$co 1620 cm$^{-1}$
NMR (D$_2$O) δ: 0.8–1.9(m, 13H), 3.4–3.9(m, 9H), 4.4–4.7(m, 1H)

EXAMPLE 1

(2RS, 3S)-3-{N-[2-(1-Naphthylmethyl)-3-(morpholinocarbonyl)propionyl]-L-histidyl)amino-4-cyclohexyl-2-hydroxybutyric acid isopropyl ester (Compound A)

To a solution of 100 mg of N-[2-(1-naphthylmethyl)-3-(morpholinocarbonyl)propionyl]-L-histidine hydrazide in 5 ml of N,N-dimethylformamide were added successively a solution of 0.12 ml of a 5.95N-dry hydrogen chloride in N,N-dimethylformamide and 0.043 ml of isoamyl nitrite at −20° C. with stirring. After disappearance of the hydrazide compound, the reaction mixture was cooled to −30° C., and then neutralized by adding 0.10 ml of triethylamine to prepare a solution of N-[2-(1-naphthylmethyl)-3-(morpholinocarbonyl)propionyl]-L-histidine azide. The azide solution was added to a solution of 58 mg of (2RS, 3S)-3-amino-4-cyclohexyl-2-hydroxybutyric acid isopropyl ester hydrochloride and 0.064 ml of triethylamine in 2 ml of N,N-dimethylformamide with stirring under ice-cooling, and then the mixture was still stirred for 16 hours. To the reaction mixture was added a 5% aqueous sodium bicarbonate solution, and the mixture was extracted with ethyl acetate. The ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methyl alcohol =5/1 by volume) to obtain 55 mg of (2RS, 3S)-3-{N-[2-(1-naphthylmethyl)-3-(morpholinocarbonyl)propionyl]-L-histidyl-}amino-4-cyclohexyl-2-hydroxybutyric acid isopropyl ester having an $Rf_2$ value of 0.50 as a white powder.

melting point: 103°–106° C.
$Rf_1$: 0.60
$Rf_2$: 0.50

MS: MH+, 690

EXAMPLE 2

(2RS, 3S)-3-{N-[2-(1-Naphthylmethyl)-3-(morpholinocarbonyl)propionyl]-L-histidyl}amino-4-cyclohexyl-2-hydroxy-N-isobutylbutyramide (Compound B)

To a solution of 100 mg of N-[2-(1-naphthylmethyl)-3-(morpholinocarbonyl)propionyl]-L-histidine methyl ester in 5 ml of methyl alcohol was added 0.42 ml of a 1N-aqueous sodium hydroxide solution with stirring under ice-cooling, and then the mixture was stirred for 16 hours at room temperature. The reaction mixture was evaporated under reduced pressure. The residue, 61 mg of (2RS, 3S)-3-amino-4-cyclohexyl-2-hydroxy-N-isobutylbutyramide hydrochloride and 43 of 1-hydroxybenzotriazole were dissolved in 5 ml of N,N-dimethylformamide, and to the solution was added 48 mg of dicyclohexylcarbodiimide with stirring under ice-cooling. The mixture was stirred for 16 hours at room temperature. The reaction mixture was evaporated under reduced pressure, and to the residue was added a 5% aqueous sodium bicarbonate solution. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methyl alcohol=5/1 by volume) to obtain 6.5 mg of (2RS, 3S)-3-{N-[2-(1-naphthylmethyl)-3-(morpholinocarbonyl)propionyl]-L-histidyl}amino-4-cyclohexyl-2-hydroxy-N-isobutylbutyramide as a white powder.

melting point: 119°-125° C.
$Rf_1$: 0.54
$Rf_2$: 0.41
MS: MH+, 703

EXAMPLE 3

(2RS, 3S)-3-{N-[2-(1-Naphthylmethyl)-3-(morpholinocarbonyl)propionyl]-L-histidyl)amino-4-cyclohexyl-2-hydroxybutyric acid cyclopentyl ester (Compound C)

To a solution of 100 mg of N-[2-(1-naphthylmethyl)-3-(morpholinocarbonyl)propionyl]-L-histidine methyl ester in 1 ml of methyl alcohol was added 0.20 ml of a 1N-aqueous sodium hydroxide solution with stirring under ice-cooling. The mixture was stirred for 1 hour under ice-cooling, and then stirred for 14 hours at room temperature. The reaction mixture was evaporated under reduced pressure. To a solution of the residue and 55 mg of (2RS, 3S)-3-amino-4-cyclohexyl-2-hydroxybutyric acid cyclopentyl ester hydrochloride in 2 ml of N,N-dimethylformamide were added 0.046 ml of diphenylphosphoryl azide and 0.030 ml of triethylamine with stirring under ice-cooling, and then the mixture was stirred for 14 hours under ice-cooling. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydous magnesium sulfate, and evaporated under reduced pressure. The residue was purified by preparative silica gel thin layer chromatography (developing solvent: chloroform/methyl alcohol =5/1, by volume) to obtain 41 mg of (2RS, 3S)-3-{N-[2-(1-naphthylmethyl)-3-(morpholinocarbonyl)propoionyl]-L-histidyl-}amino-4-cyclohexyl-2-hydroxybutyric acid cyclopentyl ester having an $Rf_2$ value of 0.58 as a white powder.

melting point: 95°-100° C.
$Rf_1$: 0.59
$Rf_2$: 0.58
MS: MH+, 716

EXAMPLE 4

The following compounds were prepared in an analogous manner to that described in Example 3.

(2R, 3S)-3-{N-[2-(1-Naphthylmethyl)-3-(morpholinocarbonyl)propionyl]-L-histidyl}amino-4-cyclohexyl-2-hydroxybutyric acid isopropyl ester (Compound D)

White powder
melting point: 99°-104° C.
$Rf_1$: 0.60
$Rf_2$: 0.50
MS: MH+, 690

(2RS, 3S)-3-{N-[2-(1-Naphthylmethyl)-3-(morpholinocarbonyl)propionyl]-L-histidyl}amino-4-cyclohexyl-2-hydroxybutyric acid cyclohexyl ester (Compound E)

White powder
melting point: 110°-115° C.
$Rf_1$: 0.59
$Rf_2$: 0.58
MS: MH+, 730

4-[(2RS, 3S)-3-{N-[2-(1-Naphthylmethyl)-3-(morpholinocarbonyl)propionyl]-L-histidyl}amino-4-cyclohexyl-2-hydroxybutyryl]morpholine (Compound F)

White powder
melting point: 118°-125° C.
$Rf_1$: 0.57
$Rf_2$: 0.51
MS: MH+, 717

(2RS, 3S)-3-{N-[2-(1-Naphthylmethyl)-3-(morpholinocarbonyl)propionyl]-L-histidyl}amino-4-cyclohexyl-2-hydroxybutyric acid 1,3-difluoro-2-propyl ester (Compound G)

White powder
melting point: 116°-122° C.
$Rf_1$: 0.57
$Rf_2$: 0.53
MS: MH+, 726

TEST EXAMPLE 1

Inhibitory effect on human renin-sheep renin substrate reaction system in vitro

To a mixture of 200 μl of a 125 mM pyrophosphate buffer (pH 7.4) containing 5 mM EDTA.2Na and a 0.1% neomycin sulfate, 25 μl of a 20 mM L-phenylalanyl-L-alanyl-L-proline as an angiotensin converting enzyme inhibitor, 50 μl of semipurified sheep renin substrate (2000 ng angiotensin I:eq./ml), 50 μl of dimethyl sulfoxide solution of an amino acid derivative of the present invention and 150 μl of deionized water was added 25 μl of purified human renin (20-30 ng angiotensin I/ml/hr). The mixture was incubated for 15 minutes on a water bath at 37° C., and the reaction mixture was allowed to stand for 5 minutes on a water bath at 100° C. to stop the reaction. After cooling, 200 μl of the solution was taken up and the amount of angiotensin I produced by the addition of renin was determined by radioimmunoassay using renin riabead kit (DAINABOT).

The inhibitory effect was calculated by the following equation.

As a control, the same procedure as above was carried out by using 50 μl of dimethyl sulfoxide alone in place of the 50 μl of dimethyl sulfoxide solution containing an amino acid compound of the present invention.

Inhibition (%) =

$$\frac{\text{Amount of angiotensin } I \text{ in control} - \text{Amount of angiotensin } I \text{ in a mixture containing a compound of the present invention}}{\text{Amount of angiotensin } I \text{ in control}} \times 100$$

The molar concentration producing a 50% inhibition (IC$_{50}$) was calculated from the inhibition values obtained, and the results are shown below.

| Compound | IC$_{50}$ molar concentration |
|---|---|
| A | $6.5 \times 10^{-9}$ |
| B | $2.9 \times 10^{-7}$ |
| C | $2.5 \times 10^{-9}$ |
| D | $2.4 \times 10^{-9}$ |
| E | $6.6 \times 10^{-9}$ |
| F | $3.7 \times 10^{-7}$ |
| G | $2.9 \times 10^{-9}$ |

TEST EXAMPLE 2

Renin inhibitory effect in a human high renin plasma

A mixture of 350 μl of a 0.5 M phosphate buffer (pH 7.0) containing 14 mM EDTA.2Na and a 0.3% neomycin sulfate, 50 μl of a 20 mM L-phenylalanyl-L-alanyl-L-proline as an angiotensin converting enzyme inhibitor and 100 μl of dimethyl sulfoxide solution containing an amino acid derivative of the present invention was added to 500 μl of human high renin plasma. Two hundred μl of the mixture was placed on an ice bath, at 4° C., and remaining mixture (800 μl) was incubated for 60 minutes at 37° C. on a water bath. Two hundred μl of the incubated remaining mixture was chilled immediately on an ice bath, and the amount (A) of angiotensin I produced was determined by radioimmunoassay using renin riabead kit (DAINABOT).

The amount (B) of angiotensin I in the mixture placed on an ice bath at 4° C. was also determined by radioimmunoassay.

As a control, the same procedure as above was carried out by using 100 μl of dimethyl sulfoxide alone in place of 100 μl of dimethyl sulfoxide solution containing an amino acid compound of the present invention.

The net amount was estimated as the difference between A and B.

The inhibitory effect was calculated by the following equation.

Inhibition (%) =

$$\frac{\text{Amount of angiotensin } I \text{ in control} - \text{Amount of angiotensin } I \text{ in a mixture containing a compound of the present invention}}{\text{Amount of angiotensin } I \text{ in control}} \times 100$$

The molar concentration producing a 50% inhibition (IC$_{50}$) was calculated from the inhibition values obtained, and the results are shown below.

| Compound | IC$_{50}$ (molar concentration) |
|---|---|
| A | $1.0 \times 10^{-8}$ |
| B | $2.6 \times 10^{-7}$ |
| C | $6.8 \times 10^{-9}$ |
| D | $4.7 \times 10^{-9}$ |
| E | $3.0 \times 10^{-8}$ |
| F | $1.3 \times 10^{-7}$ |
| G | $4.1 \times 10^{-9}$ |

TEST EXAMPLE 3

Renin inhibitory effect in plasma on common marmoset

The experiment was carried out by using common marmoset as described in K. G. Hofbauer et al., *Clinical and Experimental hypertension*, Vol. A5, Nos. 7 & 8 (1983), pages 1237–1247.

Furosemide was administered orally three times to common marmoset having a lower salt diet at 15 mg per Kilogram per day every other day to create a high renin state. The experiment was carried out on the third day after the last furosemide dose.

Measurement

Conscious female and male marmosets weighing 335 to 375 g were placed into small restraining chair, and by using a catheter into the femoral artery, blood collecting was carried out at intervals of 20, 40, 60, 120, 180 and 300 minutes.

Collected blood samples were centrifuged at 1200 g for 15 minutes at 4° C. Two hundred μl of the plasma was taken up and incubated for 60 minutes at 37° C., and the plasma renin activity was measured by radioimmunoassay using renin riabead kit (DAINABOT).

Compound A of this invention was dissolved in dilute hydrochloric acid, and administered orally at single dose of 30 mg/kg using catheter.

The results obtained are shown below.

| | Inhibition percent of plasma renin activity | Number of animals used |
|---|---|---|
| 20 minutes after administration | 68.2 | 3 |
| 40 minutes after administration | 88.1 | 3 |
| 60 minutes after administration | 87.1 | 3 |
| 120 minutes after administration | 88.8 | 3 |
| 180 minutes after administration | 79.6 | 3 |
| 300 minutes after administration | 53.4 | 2 |

TEST EXAMPLE 4

Hypotensive effect in marmoset

The experiment was carried out by using common marmoset as described in K. G. Hofbauer et al., *Clinical and Experimental Hypertension*, Vol. A5, Nos. 7 & 8 (1983), pages 1237–1247.

Furosemide was administered orally three times to common marmoset at 15 mg per kilogram per day every other day to create a high renin state. Blood pressure of conscious marmoset was measured on the third day after the last furosemide dose.

Measurement of blood pressure

A conscious male marmoset weighing 460 g was placed into small restraining chair. Blood pressure was measured on the tail cuff method using pretismograph. Compound C was dissolved in dilute hydrochloric acid, and administered orally at 30 mg/kg by using a catheter. The result obtained is shown below.

| Time after administration (hours) | Blood pressure (mmHg) |
|---|---|
| Control | 89.3 |
| 0.5 | 78.0 |
| 1 | 73.3 |
| 2 | 66.0 |
| 3 | 71.0 |
| 5 | 71.8 |
| 7 | 71.7 |

What is claimed is:

1. Amino acid derivatives represented by formula (I):

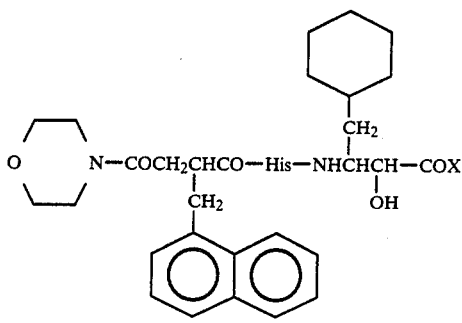

wherein His represents an L-histidyl group, X represents a straight or branched alkoxy group having 1 to 7 carbon atoms, a straight or branched alkylamino group having 1 to 7 carbon atoms, a cycloalkyloxy group having 3 to 7 carbon atoms, a morpholino group, said alkoxy group having one or more halogen atoms as substituents; or a pharmaceutically acceptable salt.

2. Amino acid derivatives as claimed in claim 1, represented by formula:

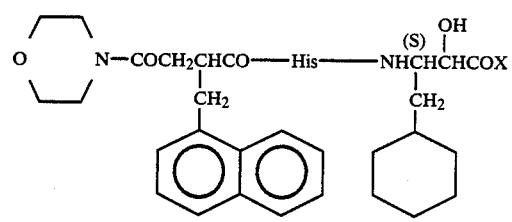

wherein (S) represents S-configuration, His and X have the same meanings as defined in claim 1 or a pharmaceutically acceptable salt thereof.

3. The amino acid derivative as claimed in claim 2, represented by formula:

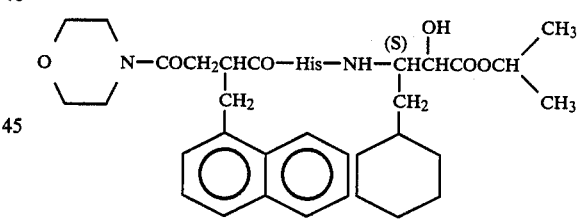

wherein His and (S) have the same meanings as defined in claim 1, or a pharmaceutically acceptable salt thereof.

* * * * *